(12) United States Patent
Kronestedt et al.

(10) Patent No.: US 7,896,850 B2
(45) Date of Patent: Mar. 1, 2011

(54) DEVICE FOR DELIVERING MEDICAMENT

(75) Inventors: Victor Kronestedt, Stockholm (SE);
Lennart Brunnberg, Tyresö (SE);
Stephan Olson, Stockholm (SE)

(73) Assignee: Telefonaktiebolaget L M Ericsson (publ), Stockholm (SE)

( * ) Notice: Subject to any disclaimer, the term of this patent is extended or adjusted under 35 U.S.C. 154(b) by 721 days.

(21) Appl. No.: 11/916,078

(22) PCT Filed: May 22, 2006

(86) PCT No.: PCT/SE2006/050148
§ 371 (c)(1),
(2), (4) Date: Jan. 10, 2008

(87) PCT Pub. No.: WO2006/130098
PCT Pub. Date: Dec. 7, 2006

(65) Prior Publication Data
US 2009/0308386 A1    Dec. 17, 2009

Related U.S. Application Data

(63) Continuation-in-part of application No. 11/140,989, filed on Jun. 1, 2005, now abandoned, which is a continuation-in-part of application No. 11/282,593, filed on Nov. 21, 2005.

(30) Foreign Application Priority Data

Jun. 1, 2005    (EP) .................................. 05104734

(51) Int. Cl.
A61M 5/00    (2006.01)
A61M 5/20    (2006.01)
A61M 5/315   (2006.01)

(52) U.S. Cl. ..................... 604/211; 604/135; 604/224

(58) Field of Classification Search .................. 604/68, 604/71, 134–137, 192, 197, 198, 207–211, 604/223, 224
See application file for complete search history.

(56) References Cited

U.S. PATENT DOCUMENTS

| | | |
|---|---|---|
| 5,104,380 A | 4/1992 | Holman et al. |
| 5,320,609 A | 6/1994 | Haber et al. |
| 5,478,316 A | 12/1995 | Bitdinger et al. |
| 2002/0120235 A1 * | 8/2002 | Enggaard .................... 604/135 |

FOREIGN PATENT DOCUMENTS

| | | |
|---|---|---|
| EP | 0338806 A2 | 10/1989 |
| EP | 1351732 B1 | 10/2003 |
| WO | 02053214 A1 | 7/2002 |

OTHER PUBLICATIONS

PCT International Search Report, mailed Sep. 6, 2006, in connection with International Application No. PCT/SE2006/050148.

* cited by examiner

*Primary Examiner*—Nicholas D Lucchesi
*Assistant Examiner*—Nathan R Price
(74) *Attorney, Agent, or Firm*—Potomac Patent Group PLLC

(57) ABSTRACT

The present invention relates to a device for the delivery of predetermined doses of liquid medicament to a patient, which medicament is intended to be inhaled by the patient or intended to be injected into the body of the patient. The device is adapted to be in a medicament delivery state and in a medicament non-delivery state. When the device is in a medicament delivery state, said device is adapted to drive a piston into a cartridge containing the liquid medicament to be delivered, with a predetermined force value. The device is designed and arranged to ensure that the predetermined dose of medicament expelled from the cartridge has a high degree of accuracy and to show the user in a simple manner how much medicament is remaining in the cartridge after a dose or several doses has/have been expelled and at the same time offering a shorter device, which is more convenient for the user when he/she has to carry it with him/her.

16 Claims, 4 Drawing Sheets

DEVICE FOR DELIVERING MEDICAMENT

TECHNICAL FIELD

The present invention relates to a device for the delivery of predetermined doses of liquid medicament to a patient, which medicament is intended to be inhaled by the patient or intended to be injected into the body of the patient or be dispensed to or for the patient. The device is adapted to be in a medicament delivery state and in a medicament non-delivery state. When the device is in a medicament delivery state, said device is adapted to drive a piston into a cartridge containing the liquid medicament to be delivered, with a predetermined force value. Said force is preferably above or equal to a predetermined minimum force value and below a predetermined maximum force value.

BACKGROUND ART

The development of devices for delivering liquid medicament to a patient, have during the recent years become more and more directed towards the ability for the patient themselves to administer the medicament with a predetermined dose in an easy, safe and reliable way and also to facilitate the administration of medicaments for hospital personnel in the same facilitated way. Depending on the intended use and type of medicament, they have developed a varying degree of automatic functions.

Currently existing automatic medicament delivery devices, conventionally comprise a cartridge or the like, containing the liquid medicament to be delivered. Said conventional delivery device is further provided with a plunger rod that is adapted to be in contact with a piston provided inside the cartridge. Upon delivery of the medicament contained in the cartridge, the plunger rod will exert a force upon the piston, whereupon the piston will move forward inside the cartridge and thus expel the medicament from the cartridge. The distance that the piston moves inside the cartridge, determines the amount of medicament to be delivered.

The force that is applied to the piston during medicament delivery is generally accomplished by means of having a pre-tensed helical spring connected to the plunger rod and thus provided in the interior of the delivery device, wherein the force is obtained in accordance with Hooke's law (1):

$$F = -k*y \quad (1)$$

wherein F is the force exerted by the spring (N), y is the displacement of the spring from its original position (m) and k is the spring constant (N/m).

From Hookes law follows that the force acting on the piston will decline linearly as the piston moves forward in the cartridge. Thus, when a large volume of medicament is to be expelled from the cartridge, the force needs to be initially high in order to be able to move the piston all the way down to the required position of the piston in the cartridge. However, the conventional cartridge is often made of an easily breakable material, such as glass, and having an initial high force acting on the piston will result in that there is a substantial risk of damaging the cartridge, which is most undesirable.

Having for instance a high viscosity medicament contained in the cartridge or having a fine needle attached to the delivery device will also require a higher force to act on the piston. The same applies for situations when the medicament is to be delivered within a short period of time. One can generally say that when a plunger rod is allowed to freely act on the piston, there is a substantial risk of damaging the cartridge when the piston is applied with a force that is above or equal to approximately 50-60 N.

One solution to the problem is to provide the delivery device with a spring having a smaller spring constant, i.e. the gradient in the force-way diagram will have more flat appearance and the initial force acting on the piston will be decreased. However, a smaller spring constant would require a larger spring and hence a larger device. A larger device is generally not handled as easily as a device with a smaller size. Another problem is, that there is a minimum force value required to initially act on the piston in order for the piston to start the movement from its original position in the distal end of the cartridge, which minimum force in the art often is referred to as the "break loose force". This force would not be obtained if the device was provided with a spring having a too small spring constant.

Also, the force acting on the piston is higher during the beginning of the medicament delivery procedure than towards the end, which results in that the piston moves faster in the beginning than in the end of said procedure, i.e. the medicament is during the procedure delivered to the patient at a higher rate in the beginning than in the end. This is undesirable, especially when the medicament is to be inhaled by the patient. This phenomena also results in that the rate with which the medicament is delivered may differ from one dose to another, since a higher dose requires an initially higher force to act on the piston than a lower dose, i.e. the so called "dose-to-dose accuracy" is poor with prior art automatic delivery devices.

Moreover, the conventional cartridge does not always have a smooth interior surface but may exhibit irregularities or unevenness as a result from the manufacturing procedure or as a result from the lubrication procedure, since the interior of the conventional cartridge most often is lubricated before use, for instance by the use of silicon oil. Such an irregularity or unevenness may increase the travel resistance acting on the piston which may cause the piston to slow down or even get stuck before it has reached its predetermined position inside the cartridge, especially if the irregularity is to be found towards the end of the distance that the piston is required to travel when the force acting on it has declined to a low value. It is generally known in the art that the force acting on the piston should not be below approximately 5 N, which thus is the lowest sliding force value needed in order not to allow the piston to get stuck before the entire set dose has been delivered.

Another problem is that the conventional delivery devices are generally made of plastic material due to manufacturing and economical reasons. Having a pre-tensed spring provided in the interior of such a device, results in that the tension caused by the pre-tensed spring, is held back by means of plastic components, which can lead to creep and hence plastic deformation of the plastic materials. This may reduce the life of the device and affect its accuracy and may also affect the automatic delivery function of said device. Also, having a high force acting on the piston during medicament delivery can cause damage of the plastic components of the device, which thus is another reason why it is not suitable to have a too high force applied to the piston, besides the risk of damaging the cartridge.

It is also important that the user of the delivery device is able to set the amount of medicament that is to be delivered in a relatively easy and reliable way. Likewise it is important and highly desired that such a delivery device is able to target specific time limits, for instance a predetermined injection time or deliver a dose within a determined time range.

Since these automatic medicament delivery devices have to be carried by the users in their pockets or their purses, it is also important that these devices are as smaller and shorter as possible.

U.S. Pat. No. 5,478,316 (Bitdinger et al) describes a device for automatic injection of a material into the body. In order to avoid the high impact of prior art devices, the device is provided with a constant force spring for moving a syringe assembly with respect to a housing and towards the skin of the patient, and for urging a rod in the direction of a piston provided inside a cartridge. The force exerted by the constant force spring is said to be sufficient to overcome the friction between the piston and the cartridge and between the needle and the user's skin.

Even though U.S. Pat. No. 5,478,316 describes the avoidance of a high impact, the device disclosed is not provided with means in order to set the force exerted on the rod to a predetermined force value, thus the advantage of applying a force to the rod that is within a predetermined force range is not described. Moreover, the device is not provided with means in order to set a predetermined dose of medicament to be delivered having a high degree of accuracy.

Devices which can be automatically expressed the dose on demand and offer a repeatable dose have been desirable the recent years. This has been described in:

The U.S. Pat. No. 5,104,380 patent by a syringe device comprising a body and a rotatable dose setting device mounted on the body and capable of being moved to a selected set position, a latch arranged to retain the setting device in the set position, and means arranged to release the latch to cause the set dose to be expelled. Movement of the dose setting device to the selected set position is accompanied by rotational straining of a spring, which, when the latch is released, provides the force for expelling the set dose. When the latch is released, the setting device is returned to an original position to drive a plunger through a one-way clutch to expel the set dose. The disclosed driving means comprises a quick pitch screw thread arrangement for transforming rotation of the setting device into linear movement of the plunger. The body is adapted for receiving a cartridge containing a fluid to be injected by having a cartridge container removable from the body for insertion of a cartridge and then removal of the cartridge container is arranged to release the quick pitch screw thread device thus allowing the plunger to be returned to an initial position; and in the EP1 351 732 B1 patent by a medicine dosage setting device for use in combination with fluid medicament containers, wherein the dose setting device comprises a housing, a drive member, a spring means, a dose setting assembly and releasable latch means. The dose setting assembly comprises a dose setting member being moveable in a first direction to a selected set position against the bias of the spring means, wherein movement of the dose setting member is accompanied by straining of the spring. The dose setting member can also be moveable in a second direction to selectively adjust the set position. The releasable latch means are associated with the housing and adapted to retain the dose setting member in the set position against the bias of the spring means. Further the release of the latch means causes the dose setting assembly to drive the drive member by the spring means to thereby expel a set dose from a fluid medicament container when the dose-setting device is used in combination therewith.

However, not all these automatic medicament delivery devices offer the opportunity to expel a predetermined volume of medicament having a high degree of accuracy and show the user in a simple manner how much medicament is left after a dose or several doses have been expelled and at the same time offering a shorter device.

SUMMARY OF THE INVENTION

The object of the present invention is therefore to provide an automatic liquid medicament delivery device, which during medicament delivery applies a force with a predetermined force value to a piston, which ensures that a predetermined volume of medicament having a high degree of accuracy is expelled from a cartridge and shows the remaining amount of medicament in the cartridge.

With the present invention it also possible to set the predetermined dose that is to be delivered in an easy and reliable way.

Another object of the present invention is to provide an automatic liquid medicament delivery device, which substantially reduces the problems with creep in and plastic deformation of the plastic materials of the delivery device.

A further object of the present invention is to overcome other shortcomings and problems of the medicament delivery devices heretofore available in the industry discussed above.

These objects are accomplished with a delivery device according to the preamble of the independent claim provided with the features according to the characterizing portions of the independent claims.

According to an aspect of the present invention, there is provided a device for delivery of predetermined doses of liquid medicament, which device is adapted to be in a medicament delivery state and in a medicament non-delivery state, said device is adapted to comprise:

a cartridge housing comprising a cartridge adapted to contain the liquid medicament and a piston sealingly and slidably arranged in said cartridge, a proximal part provided with a thread in its exterior surface and a distal part comprising a dose setting member with a thread in its interior surface and adapted to be screw threaded on the proximal part of the device to set a volume dose, an energy accumulating member adapted to accumulate energy in terms of at least one predetermined step when the device is in the medicament non-delivery state, an elongated threaded plunger rod adapted to be screwed into the cartridge housing, wherein the proximal end of the plunger rod is adapted to be in contact with the piston, such that, when the predetermined accumulated energy is adapted to be transferred to the threaded plunger rod when the device is in the medicament delivery state, the plunger rod and the piston moves towards the proximal end of the cartridge with a predetermined distance and expels a predetermined dose of the liquid medicament from the cartridge, wherein the device comprises a further energy accumulating member adapted to accumulate further energy in terms of at least one predetermined step when the dose setting member moves linearly along the exterior surface of the proximal part of the device which is provided with a remaining dose indicator means and wherein the device becomes shorter, wherein the predetermined further energy is adapted to be transferred to the threaded plunger rod so that said plunger rod is provided with a torque that helps to drive the plunger rod and the piston the predetermined distance towards the proximal end of the cartridge when the device is in the medicament delivery state, whereby the finer the pitch of grooving, or screw pitch, of the threaded components, the higher degree of accuracy will be achieved when delivering high doses.

This solution substantially lowers the risk of damaging the cartridge and/or the device, avoids the risk that the whole system stops during medicament delivery, improves the dose and the dose-to-dose accuracy in comparison with prior art devices and show the user in a simple manner how much medicament is left after a dose or several doses have been expelled and at the same time offering a shorter device, which is more convenient for the user when he/she has to carry it with him/her.

In the preferred embodiment the above effect is achieved by:

- having the elongated threaded plunger rod as a hollow elongated threaded plunger rod provided in its hollow interior with the energy accumulating member in the form of a helical plunger rod spring;
- having the further energy accumulating member as a servo drive spring in the form of e.g. a flat spiral spring, provided with outer holding means in order to be connected to the back cover and adapted to be housed in a housing member, wherein the interior of the housing member is provided with inwardly protruding means that engages longitudinal extending means on the plunger rod so that the housing member can travel along the longitudinal axis of the plunger rod when the device is in medicament delivery state;
- having the plunger rod adapted to be housed and engaged within a wheel that is provided in the interior of the device distal to the distal end of the cartridge housing, wherein the interior part of the wheel engaging the plunger rod is provided with means that engages longitudinal extending means on the plunger rod so that the wheel can travel along the longitudinal axis of the plunger rod when the device is in medicament delivery state;
- having the wheel and the housing member adapted to be in a rotating state when the device is in a medicament delivery state and adapted to be in a non-rotating state when the device is in a medicament non-delivery state and providing the wheel with protruding teeth, which teeth are adapted to engage stopper means of a needle shield or its extension to hold the dose setting member in a set volume dose position wherein by pushing the needle shield towards the distal end of the delivery device, the stopper means come out of engagement and the plunger rod that is provided with the force from the helical plunger rod spring, is screwed through the cartridge housing into the cartridge to deliver the set volume dose.

Moreover, according to another aspect of the present invention, there is provided a device for delivery of predetermined doses of liquid medicament wherein the device during medicament delivery is adapted to be set in the medicament non-delivery state before the entire set dose has been delivered, whereupon the plunger rod stops its movement towards the proximal end of the cartridge, and that the device thereafter is adapted to be set in the medicament delivery state, whereupon the plunger rod continues to move the predetermined distance towards the proximal end of the device to complete the set dose one or more times.

According to another aspect of the present invention, there is provided a device for delivery of predetermined doses of liquid medicament wherein the device is adapted to be connected to a medicament administrating member in the form of a mouth or nasal piece, which the patient puts in the mouth or nose, respectively, whereby the predetermined dose of medicament is inhaled by the patient when the delivery device is in the medicament delivery state.

According to another aspect of the present invention, there is provided a device for delivery of predetermined doses of liquid medicament wherein the device is adapted to be connected to a medicament administrating member in the form of a nozzle, whereby the predetermined dose of medicament is sprayed to the eye or onto the skin of the patient when the delivery device is in the medicament delivery state.

According to another aspect of the present invention, there is provided a device for delivery of predetermined doses of liquid medicament wherein the device is adapted to be connected to a medicament administrating member in the form of a member that deliver the predetermined dose of medicament e.g. to the eye of a patient or a in a glass/cup, in the form of at least one drop when the delivery device is in the medicament delivery state.

According to another aspect of the present invention, there is provided a device for delivery of predetermined doses of liquid medicament wherein the device is adapted to be connected to a medicament administrating member in the form of a needle for the injection of the predetermined dose of medicament into the body of the patient when the delivery device is in the medicament delivery state.

DETAILED DESCRIPTION OF THE PREFERRED EMBODIMENT OF THE PRESENT INVENTION

Figure 1:
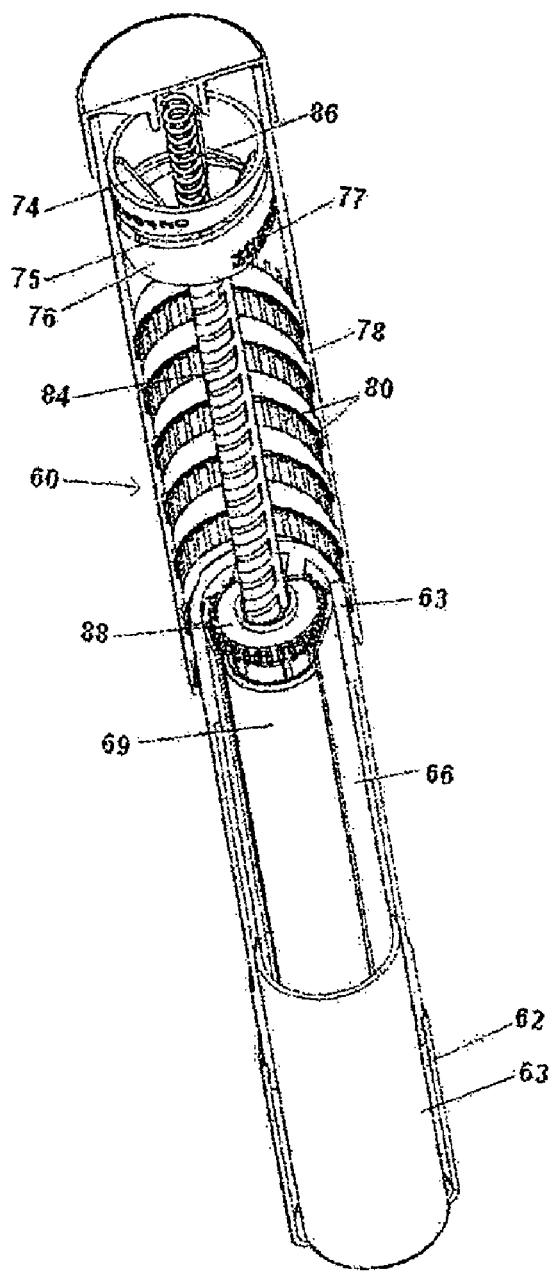
FIG. 1 illustrates the delivery device partly in cross-section.
Figure 2:
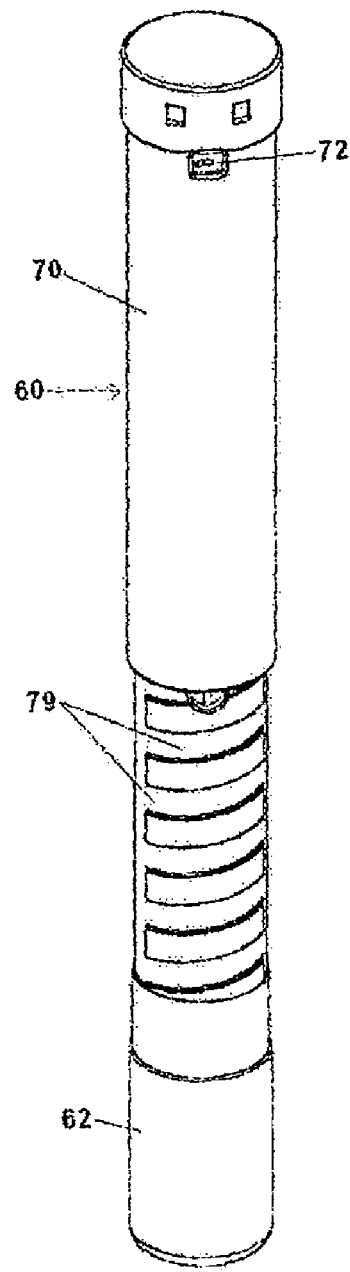
FIG. 2 illustrates an elevation view of the device.

In the present application, when the term "distal part/end" is used, this refers to the part/end of the delivery device, or the parts/ends of the members thereof, which under use of the delivery device, is located the furthest away from the medicament delivery site of the patient. Correspondingly, when the term "proximal part/end" is used, this refers to the part/end of the delivery device, or the parts/ends of the members thereof which under use of the delivery device is located closest to the medicament delivery site of the patient.

The delivery device 60 comprises in its proximal part a cartridge housing 66 comprising a cartridge 69. The cartridge 69 is intended to be filled with the liquid medicament to be administered to the patient and the delivery device is thus provided with means in order to be connected to a suitable medicament administrating member, provided with corresponding means (not shown). The medicament administrating member of the present invention is preferably a needle for the injection of a liquid medicament into the body of the patient, wherein the liquid can have a low as well as a high viscosity, but can also be for instance be a mouth or nasal piece, which the patient puts in his mouth or nose, respectively, whereby a metered dose of medicament is inhaled by the patient when the delivery device is set in a medicament delivery state, which will be described in further detail below. The medicament administering member can also be a member that introduces the liquid medicament to the eye of the patient, such as a suitable nozzle that sprays the medicament to the eye, or a member that deliver the medicament to the eye or in a glass/cup in the form of droplets. Naturally, a nozzle as a medicament administrating member can also be used in order to spray the medicament onto the skin of the patient.

The delivery device 60 is further in the preferred embodiment provided with a needle shield 63, the proximal end of which extends beyond the proximal ends of the cartridge components in order to protect the needle. For further protection of the delivery device, said device may also in its proximal end be provided with removable cap 62. The distal end of the needle shield or its extension is provided with inward protruding stopper means 65, the function of which will be described in further detail below.

The distal part of the delivery device comprises a dose setting member in the form of a back cover 70 provided with a dose window 72. In the interior distal part of the back cover is a hollow drum 76 arranged. The drum 76 is provided with a through going slot 75 arranged in a helical-formed pattern along the surface of the drum. The back cover is further in its distal part provided with an inward protruding pin (not shown) arranged to engage and run along the slot 75 of the drum and stop the rotation of the drum when a dose has been delivered. This rotation stop can also be arranged as a flange (not shown) on the external surface under the drum. Moreover, the external surface of the drum is circumferentially provided with for instance numerical indicators 77 which are visible for the user through a dose window 72, as described further below. The window 72 can optionally be provided with a suitable lens or the like, in order to enlarge the dose indicators for the user.

The interior surface of the back cover is provided with a thread 78 in order to be screw threaded on the proximal part of the device. The exterior surface of the proximal part of the device is thus also provided with a thread 79 that is adapted to engage the thread 78. The helical-formed configuration of the slot 75 in the drum 76 consequently corresponds to the pitch of grooving, or screw pitch, of the threads 78, 79. The thread 78 is further provided with equally distributed recesses 80 that correspond to at least one protrusion 81 on the exterior of the proximal part of the device. Alternatively, an interface (not shown) is provided between the proximal part and the distal part of the device that is provided with means that have the function of the recesses 80 and protrusions 81; see further description of said function below.

A screw threaded elongated plunger rod 84 is provided in the interior of the delivery device, running along the longitudinal axis of said device. The proximal end of the plunger rod is in contact with a piston (not shown) sealingly and slidably provided inside the cartridge 69. The plunger rod 84 is provided as a hollow member and the hollow interior of the plunger rod is provided with an energy accumulating member in the form of a helical plunger rod spring 86. The distal end of the helical spring 86 is in contact with the inner distal end of the back cover 70 and the proximal end preferably against the inner proximal end surface of the plunger rod 84. The plunger rod 84 is further fast connected to the drum 76 by e.g. means of inner connecting means 74 or manufactured as a whole piece.

Figure 3:
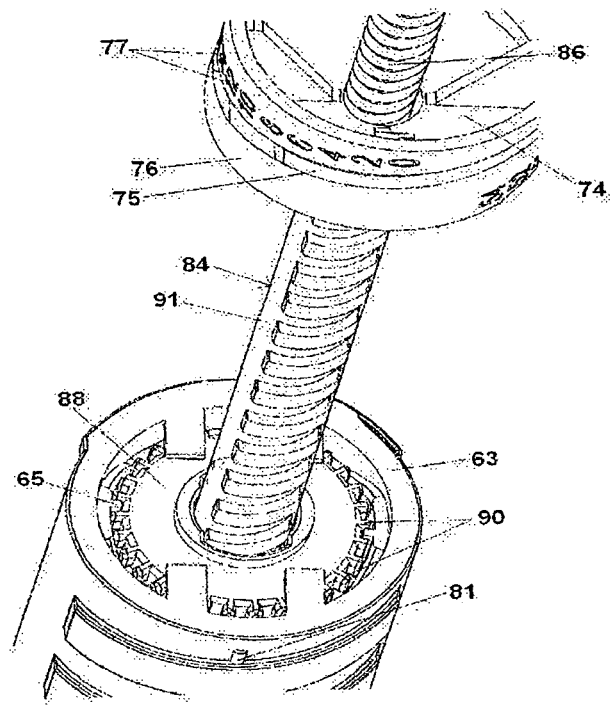
FIG. 3 illustrates in its lower part an enlarged view of the connection between the needle shield and the wheel when the device is in a medicament non-delivery state, and in its upper part an enlarged view of the dose setting member leaving out the back cover.
Figure 6:
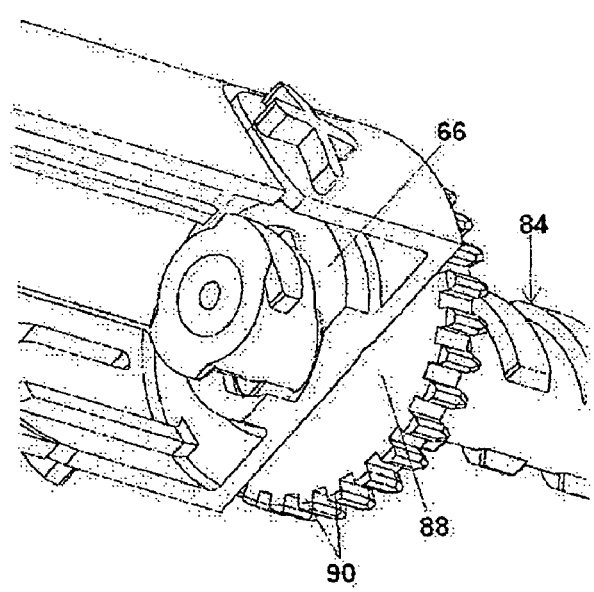
FIG. 6 illustrates an enlarged view of the connection between the plunger rod, the cartridge housing and the wheel.

The plunger rod 84 is adapted to be screwed into the cartridge housing 66 and is further adapted to be housed within a wheel 88 that is provided in the interior of the device 60 distal to the distal end of the cartridge housing, see FIG. 6. The interior part of the cartridge housing 66 that constitutes an entrance for, and is adapted to engage, the plunger rod is thus provided with a thread that has a pitch of grooving, i.e. a screw pitch, that corresponds to thread of the plunger rod. The threads 78 and 79, the thread in the interior of the cartridge housing, the thread of the plunger rod and as a logical consequence the helical formed configuration of the slot 75, all have the same predetermined pitch of grooving, or screw pitch. The wheel 88 is adapted to be in rotating state and in a non-rotating state and is therefore provided with protruding teeth 90, which teeth are adapted to engage the stopper means 65 of the needle shield 63. That is, when the delivery device 60 is in a non-medicament delivery state, as seen in FIG. 3, a stopper means 65 is provided in between two protruding teeth 90, holding the wheel in a non-rotating state, as will be described in further detail below. The interior of the wheel 88 is further provided with means that corresponds to the thread on the plunger rod, so that when the wheel 88 is in the non-rotating state, the plunger rod is prevented from rotating. Thus, when the wheel 88 is released for rotation, the plunger can be rotated and screwed into the cartridge housing. The means in the interior of the wheel 88 is thus also adapted so that the wheel can travel along the longitudinal axis of the plunger rod.

The interior of the wheel is thus provided with inwardly protruding means 92 that engages longitudinal extending means 91 on the plunger rod.

Figure 5:
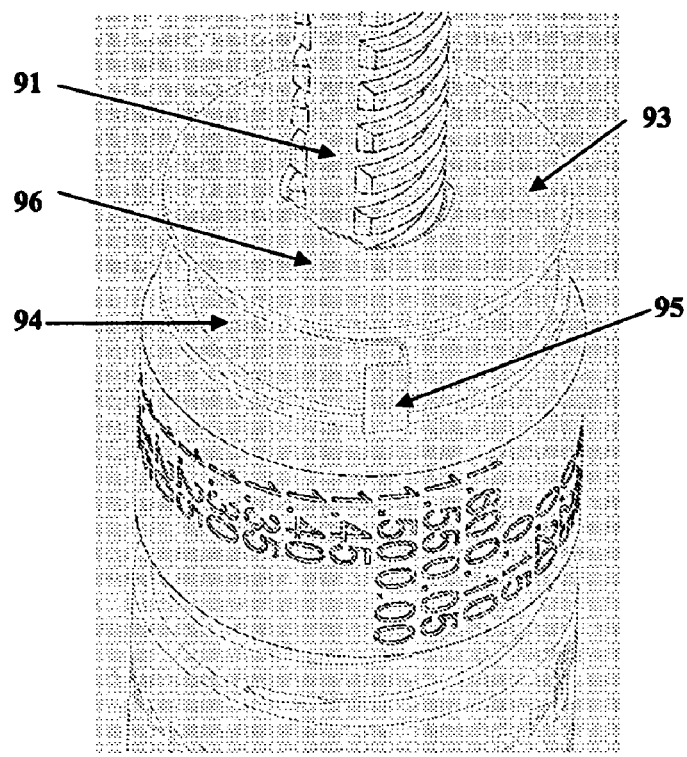
FIG. 5 illustrates an enlarged view of the connection between the plunger rod and the housing member provided with an energy accumulating member in the form of a servo drive spring.

Further, as seen in FIG. 5, the delivery device 60 comprises a housing member 93 adapted to house an energy accumulating member in the form of a servo drive spring 94. Said servo drive spring 94 is in its inner end provided with inner holding means (not shown) in order to be attached to the housing member 93, such as for instance a protruding member adapted to be fitted with a corresponding slit in the housing member 93, or alternatively a hole of a suitable size in the servo drive spring 94, and a smaller screw or other similar means for the anchoring of the servo drive spring 94 in the housing member 93.

At the outer end of the servo drive spring 94, said servo drive spring 94, e.g. a flat spiral spring, is provided with outer holding means in order to be connected to the back cover 70 of the delivery device 60. Said outer holding means comprises preferably a bend 95 of the outer end of the servo drive spring 94, which is fitted with a corresponding slit in the back cover 70.

The interior of the housing member 93 is provided with inwardly protruding means 92 that engages the longitudinal extending means 91 on the plunger rod so that the housing member 93 can travel along the longitudinal axis of the plunger rod.

The Inventive Delivery Device and the Function thereof will now be Explained in Detail According to a Preferred use thereof.

Before use, the cap 62 is removed from the device 60 and a suitable medicament administrating member is attached to the cartridge retainer, preferably a needle. Then the dose is set in a first dose delivery step by rotating the back cover 70 clock-wise. When rotating the back-cover, the pin will also run along the slot 75 of the drum 76, and the entire back cover will rotatingly move towards the proximal end of the device 60 as the thread 78 is in engagement with the thread 79. As the back cover 70 moves towards the proximal end of the device, the recesses 80 of the thread 78 slide over the corresponding protrusions 81. Each time a recess 80 slides over such a corresponding protrusion 81, the dose is increased by one step and the set dose is visible for the user of the device through the dose window 72 by the numerical indicators provide on the drum 76. If the dose is set to high, the user can easily rotate the back cover counter-clock wise and adjust the set dose. It is also possible to provide the device with means (not shown) that sets a certain dose as a default dose value, for instance by providing the slot in the drum with a stopper means at a predetermined position that prevents the pin from running along said slot a longer distance than the distance that correspond to the default dose.

As the back cover moves in steps towards the proximal end of the device 60, also the plunger rod spring 86 in the interior of the plunger rod 84 is compressed and step-wise accumulates a spring force corresponding to the predetermined distance that the back cover 70 moves towards the proximal end of the device 60. The higher dose set, the greater spring force accumulated in the spring 86.

If a the device is using a plunger rod 84 having a very fine pitch of grooving, or screw pitch, to give a very accurate dose and at the same time the device must be set to give a high dose; then a great force will be accumulated in the spring 86, which will press the threads of the plunger rod against the threads of the cartridge housing when the device is in a medicament delivery state. Since the threaded components have a very fine of pitch of grooving and the force accumulated in the spring is very high, the device could stop the movement of the plunger rod before the whole set dose has been delivered. To avoid this, a servo spring 94 is designed and arranged to the device. Said servo spring 94 will provided the plunger rod with a torque that helps to drive the plunger rod when the device is in the medicament delivery state.

As the dose is set in a first dose delivery step by rotating the back cover 70 clock-wise, the outer holding means 95 of the servo drive spring 94, engaged to the to the back cover 70, will rotate correspondingly and hence said servo drive spring 94 is free to wind up and accumulate energy corresponding to the rotation of the back cover 70.

Figure 4:
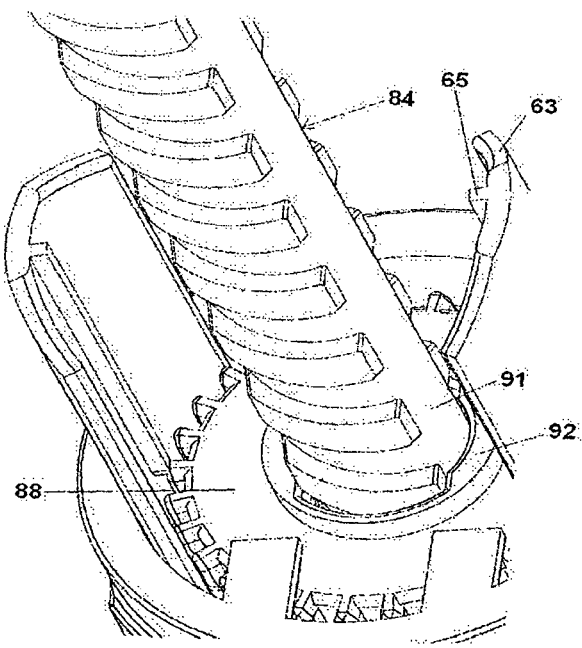
FIG. 4 illustrates an enlarged view of the connection between the needle shield and the wheel when the delivery device is in a medicament delivery state.

The delivery device 60 is now ready to in a second dose delivery step be set in a medicament delivery state. This is accomplished by pushing the needle shield 63 towards the distal end of the delivery device, preferably by pushing the proximal end of the needle shield 63 against the patient's skin at the medicament delivery site. When the needle shield moves towards the distal end of the delivery device, the stopper means 65 of the needle shield come out of engagement with the teeth 90 of the wheel 88, as seen in FIG. 4. Due to the accumulated spring force both in the plunger rod spring 86 and in the servo drive spring 94 during the first dose delivery step, the plunger rod will now, provided with the force from both the spring 86 and the spring 94, be screwed into the cartridge housing and moves thus towards the proximal end of the device. Since the proximal end of the plunger rod is in contact with the piston sealingly provided inside the cartridge 69, said piston will move a predetermined distance towards the proximal end of the cartridge 69 and deliver the set volume dose. The predetermined distance that the piston 87 moves inside the cartridge, and thus the force acting on the piston, is determined by the spring force accumulated in both the plunger rod spring 86 and the servo drive spring 94 when the dose is set as well as by the threaded design of the threaded components of the device, i.e. the threads 78 and 79, the thread in the interior of the cartridge housing and the thread on the plunger rod. The finer the pitch of grooving, or screw pitch, of the threaded components, the higher degree of accuracy will be achieved and lower the force acting on the piston. Therefore the device is designed and arranged with the servo drive spring 94. The device 60 is designed in accordance with the cartridge so that the movement of the piston the predetermined distance towards the proximal end of the cartridge will correspond to the delivery of the dose set in the first dose delivery step.

During dose delivery, when the plunger rod 84 is forced into the cartridge housing, both the wheel 88 and the housing member 93 is rotated along with the rotating plunger rod and travels along its longitudinal axis. The drum 76 is rotated and moves along with the downwards rotating plunger rod due to the connecting means 74, whereupon the dose volume to be delivered is visible for the user through the dose window 72 and counts down until the entire dose is delivered. If the cartridge is emptied before the entire dose is delivered, the dose remaining to be taken is shown in the window. The back cover will however, stay at its current position and the device thus becomes shorter every time a dose has been delivered. The exterior surface of the proximal part of the device, can thus be provided with further dose indicator means (not shown), that by means of the current position of the back cover proximal end indicates the remaining doses, i.e. the remaining amount of medicament, in the cartridge.

When the dose has been delivered the user releases the needle shield 63, by for instance simply removing the device from the injection site, whereupon the stopper means 65 once again will engage the teeth 90 of the wheel, which thus sets the delivery device 60 in a non-medicament delivery state. The plunger rod 84 will stay at its current position, with its proximal end in contact with the piston, and the delivery device is ready to be used again. Preferably the needle is removed and the cap 62 is put back on again after use.

The user of the delivery device can also release the needle shield during medicament delivery and hence set the delivery device in the medicament non-delivery state before the set dose has been delivered. The user can then once again push the needle shield towards the distal end of the device, whereby the set dose continues to be delivered. The procedure above can be repeated an optional number of times until the entire set dose has been delivered. This procedure is for instance suitable when a predetermined dose of medicament is to be delivered to a patient at multiple injection sites, whereby the user of the device moves the device from one injection site to another while the delivery device is in the medicament non-delivery state. If the delivery device needs to be primed before use, this is easily accomplished by setting a small dose volume to be delivered before the first dose delivery step and gently push the needle shield back until a small drop is seen by the end of the needle or a small jet is ejected there from.

If the delivery device 60 is used with a medicament administrating member in the form of a mouth/nasal piece, the function of the needle shield that holds and sets the wheel 88 in a non-rotating and a rotating state, respectively, can be replaced with other suitable means. Such as for instance the dose actuation member 44 described in connection with the first embodiment, that when actuated will release the wheel 88 for rotation, or a breath sensing means, i.e. the wheel is released for rotation by means of inhalation of the user. Thus, such a dose actuation member or breath sensing means is also provided with stopper means 65 with the above described function.

Figure 7:
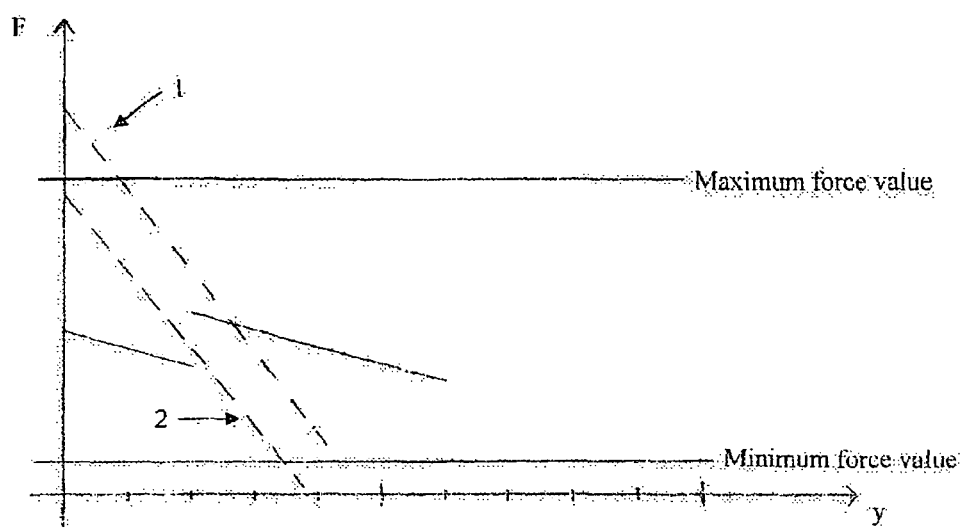
FIG. 7 illustrates graphically the force acting on the piston as a function of the traveled distance by the piston during medicament delivery in comparison with prior art devices (not to scale).

So, with the present invention, the force that drives the plunger rod towards the proximal end of the delivery device, due to the accumulated energy both in the plunger rod spring 86 and in the servo drive spring 94 and due to the threaded design of the threaded components of the device, is in an effective way set to a predetermined force value during the first dose delivery step. This set force and the force that acts on the piston is during the entire medicament delivery ensured to be above or equal to a minimum force value, which is the lowest force value needed to deliver the set predetermined dose, and is also ensured to be below a maximum force value, which is the first force value at which it exists a risk of damaging the cartridge or the device. Within this predetermined force range it is feasible to tune the device to specific desired administration times. The device is thus provided so that the maximum energy to be accumulated in both the plunger rod spring 86 and in the servo drive spring 94, in cooperation with the threaded components of the device, corresponds to a force applied to the piston that is below the maximum force value. That is to say that the device is provided with means (not shown) that prevents the user to rotate the back cover, and thus move it towards the proximal end of the device a too long distance, i.e. a distance that will accumulate an energy in the spring 86 that corresponds to a force applied to the piston that is above the maximum force value. Also, the setting of a dose corresponding to one dose increment step will accumulate energy in the springs 86 and 94 that will provide the piston, in cooperation with the threaded components of the device, with a force that is above or equal to the minimum force value. FIG. 7 graphically shows the force acting on the piston (F) as a function of the traveled distance (y) by the piston from its original position during medicament delivery, wherein the delivery device first delivers a predetermined dose corresponding to two dose increment steps and thereafter delivers a dose corresponding to four dose increment steps, the indications on the y-axis thus correspond to the dose increment steps. The inclination of the continuous lines, respectively, is identical. As seen, the force is during medicament delivery above and below, respectively, said minimum and maximum force value and the force is thus within a predetermined range. It is to be understood that the force curve obtained with the inventive device can have different appearances depending on the type of spring chosen as the energy accumulating member. The dashed lines 1 and 2 represent the force acting on the piston in a prior art delivery device provided with a helical spring as described by ways of introduction, during the delivery of an amount of medicament corresponding to four dose increment steps. With reference to dashed line 1, the initial force acting on the piston needs to be over the maximum force value in order for the piston to reach the distance in the cartridge that delivers a dose corresponding to four dose increments steps, i.e. there is a risk of damaging the cartridge. If the initial force is lowered, as seen when turning to the dashed line 2, the force acting on the piston will decrease to value below the minimum force value before the piston has reached its required position inside the cartridge and there is a risk that the piston will get stuck before the entire set dose is delivered. Thus, with the present invention, the predetermined dose is ensured to be delivered and the risk for damaging the cartridge or the device due to a too high initial force acting on the piston is substantially reduced, which is a problem with prior art automatic medicament delivery devices.

Moreover, with the present invention, the tensions resulting from both the pre-tensed helical spring and the servo drive spring provided in the interior of the delivery device are restricted to act on a few components only, i.e. restricted to act in a controlled geometric area. In that way, said components or area, can be designed accordingly, so that the problem with creep can be reduced. The problem with plastic deformation of the plastic components of the device is also reduced due to the fact that the force that is applied to the piston does not need to be initially high as with the prior art devices, due to the effective cooperation between the energy accumulating member and the threaded components of the device of the present invention. That is, having a well controlled threaded design of said components that cooperates with the force from the energy accumulating member during dose delivery, requires less force to act on the piston in comparison with prior art devices.

However, even though the present invention has been described and illustrated in detail, said description and said illustrations shall be regarded as being non limited, since it will be appreciated that only the currently preferred embodiment has been shown. For instance, the rotation directions mentioned above, can naturally be the opposite rotation direction by suitable configurations of the device that are readily carried out by the person skilled in the art, so that a counter clock-wise rotation as mentioned above instead is a clock-wise rotation, and vice versa.

60. Delivery device
62. Cap
63. Needle shield
65. Needle shield stopper means
66. Cartridge housing
69. Cartridge
70. Back cover
72. Dose window
75. Slot in drum
76. Drum
77. Numerical indicators
78. Thread in back cover
79. Thread on device
80. Recesses in thread 78
81. Protrusions corresponding to recesses 80
84. Plunger rod
86. Helical plunger rod spring
87. Piston
88. Wheel
90. Teeth of wheel
91. Longitudinal extending means on the rod
92. Interior means
93. Housing member
94. Servo drive spring

The invention claimed is:

1. A device for delivering predetermined doses of liquid medicament, the device having a medicament delivery state and a medicament non-delivery state and comprising:
   a cartridge housing including a cartridge configured to contain the liquid medicament and a piston sealingly and slidably arranged in the cartridge;
   a proximal part having a thread in its exterior surface, and a distal part including a dose setting member having a thread in its interior surface and configured to be screw-threaded on the proximal part to set a dose volume;
   an energy accumulating member configured to accumulate energy when the device is in the medicament non-delivery state;
   an elongated threaded plunger rod configured to be screwed into the cartridge housing, wherein a proximal end of the plunger rod is configured to be in contact with the piston, such that, when energy accumulated by the energy accumulating member is transferred to the plunger rod when the device is in the medicament delivery state, the plunger rod and the piston move toward a proximal end of the cartridge by a predetermined distance and expel a dose of the liquid medicament from the cartridge; and a further energy accumulating member configured to accumulate further energy when the dose setting member moves linearly along the exterior surface of the proximal part of the device which is provided with a remaining dose indicator and wherein the device becomes shorter;

wherein the further energy accumulating member is configured to transfer further energy to the plunger rod so that the plunger rod is provided with a torque that helps to drive the plunger rod and the piston the predetermined distance toward the proximal end of the cartridge when the device is in the medicament delivery state.

2. The device of claim 1, wherein a remaining amount of medicament in the cartridge is indicated by a current position of a proximal end of the dose setting member against the remaining dose indicator.

3. The device of claim 1, wherein the device becomes shorter every time a dose has been set and delivered.

4. The device of claim 2, wherein the device becomes shorter every time a dose has been set and delivered.

5. The device of claim 1, wherein the plunger rod is hollow and the energy accumulating member is a helical plunger rod spring included in the plunger rod.

6. The device of claim 2, wherein the plunger rod is hollow and the energy accumulating member is a helical plunger rod spring included in the plunger rod.

7. The device of claim 1, wherein the further energy accumulating member is a servo drive spring provided with an outer holding device in order to be connected to the back cover and configured to be housed in a housing member; an interior of the housing member is provided with an inwardly protruding device that engages a longitudinal extending device on the plunger rod so that the housing member can travel along a longitudinal axis of the plunger rod when the device is in the medicament delivery state.

8. The device of claim 1, wherein the plunger rod is further configured to be housed and engaged within a wheel that is provided in an interior of the device distal to the distal end of the cartridge housing; and an interior part of the wheel engaging the plunger rod is provided with a device that engages longitudinal extending devices on the plunger rod so that the wheel can travel along a longitudinal axis of the plunger rod when the device is in the medicament delivery state.

9. The device of claim 8, wherein the wheel and the housing member are configured to rotate when the device is in a medicament delivery state and not to rotate when the device is in a medicament non-delivery state; the wheel has protruding teeth configured to engage a stopper device of a needle shield or its extension to hold the dose setting member in a set volume dose position; by pushing the needle shield towards the distal end of the delivery device, the stopper device comes out of engagement; and the plunger rod that is provided with the force from the spring is screwed through the cartridge housing into the cartridge to deliver the set volume dose.

10. The device of claim 7, wherein the plunger rod is further configured to be housed and engaged within a wheel that is provided in an interior of the device distal to the distal end of the cartridge housing; and an interior part of the wheel engaging the plunger rod is provided with a device that engages longitudinal extending devices on the plunger rod so that the wheel can travel along the longitudinal axis of the plunger rod when the device is in the medicament delivery state.

11. The device of claim 10, wherein the wheel and the housing member are configured to rotate when the device is in a medicament delivery state and not to rotate when the device is in a medicament non-delivery state; the wheel has protruding teeth configured to engage a stopper device of a needle shield or its extension to hold the dose setting member in a set volume dose position; by pushing the needle shield towards the distal end of the delivery device, the stopper device comes out of engagement; and the plunger rod that is provided with the force from the spring is screwed through the cartridge housing into the cartridge to deliver the set volume dose.

12. The device of claim 1, wherein the device during medicament delivery is configured to be set in the medicament non-delivery state before an entire set dose has been delivered, whereupon the plunger rod stops its movement toward the proximal end of the cartridge; and the device thereafter is configured to be set in the medicament delivery state, whereupon the plunger rod continues to move the predetermined distance towards the proximal end of the device to complete the set dose one or more times.

13. The device of claim 1, wherein the device is configured to be connected to a medicament administering member that is put in a patient's mouth or nose, whereby the predetermined dose of medicament is inhaled by the patient when the device is in the medicament delivery state.

14. The device of claim 1, wherein the device is configured to be connected to a medicament administering member such that the predetermined dose of medicament is sprayed into an eye or onto a skin of a patient when the device is in the medicament delivery state.

15. The device of claim 1, wherein the device is configured to be connected to a medicament administering member that delivers the predetermined dose of medicament as at least one drop when the device is in the medicament delivery state.

16. The device of claim 1, wherein the device is configured to be connected to a medicament administering needle for injecting the predetermined dose of medicament into a body of a patient when the device is in the medicament delivery state.

* * * * *